United States Patent
Lakshmipathy et al.

(10) Patent No.: US 9,334,523 B2
(45) Date of Patent: May 10, 2016

(54) SUBSTRATES AND METHODS FOR STAINING LIVE STEM CELLS

(75) Inventors: Uma Lakshmipathy, Carlsbad, CA (US); Upinder Singh, Eugene, OR (US); Scott Grecian, Jasper, OR (US); Rene Quintanilla, Temecula, CA (US); Kyle Gee, Springfield, OR (US); Mahendra Rao, Timonium, MD (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/985,559

(22) PCT Filed: Feb. 14, 2012

(86) PCT No.: PCT/US2012/025123
§ 371 (c)(1),
(2), (4) Date: Aug. 14, 2013

(87) PCT Pub. No.: WO2012/112609
PCT Pub. Date: Aug. 23, 2012

(65) Prior Publication Data
US 2013/0323770 A1    Dec. 5, 2013

Related U.S. Application Data

(60) Provisional application No. 61/442,490, filed on Feb. 14, 2011, provisional application No. 61/576,253, filed on Dec. 15, 2011.

(51) Int. Cl.
*C12Q 1/42* (2006.01)
*G01N 33/50* (2006.01)
*G01N 33/58* (2006.01)

(52) U.S. Cl.
CPC .............. *C12Q 1/42* (2013.01); *G01N 33/5073* (2013.01); *G01N 33/582* (2013.01); *G01N 33/586* (2013.01)

(58) Field of Classification Search
None
See application file for complete search history.

(56) References Cited

U.S. PATENT DOCUMENTS

2008/0171385 A1* 7/2008 Bergendahl .......... C12N 5/0606
435/366

FOREIGN PATENT DOCUMENTS

JP    2005/058225    3/2005

OTHER PUBLICATIONS

Richards et al Nature Biotechnology, Sep. 2002, vol. 20, pp. 933-936.*
Vector Labs Protocol Sheet "Alkaline Phosphatase Statining" retrieved from internet Nov. 17, 2015; 3 pages. <https://icahn.mssm.edu/static_files/MSSM/Files/Research/Resources/Shared%20Resource%20Facilities%20(SRF)/Human%20Embryonic%20Stem%20Cell/AP_staining.pdf>.*
Molecular Probes, "Alkaline and Acid Phosphatase Substrates: FDP, MUP, DiMUP and DDAO Phospate", Manual: Product Information, Nov. 26, 2002, 1-3.
PCT/US2012/025123 International Preliminary Report on Patentability Issued Aug. 21, 2013.
PCT/US2012/025123 International Search Report and Written Opinion Mailed Aug. 14, 2012, 1-18.
Takakusa, H. et al., "A Novel Design Method of Ratiometric Fluorescent Probes Based on Fluorescence Resonance Energy Transfer Switching by Spectral Overlap", *Chem. Eur. J.*, vol. 9(7), Apr. 4, 2003, 1479-1485.

* cited by examiner

*Primary Examiner* — Allison Fox
(74) *Attorney, Agent, or Firm* — Gloria L. Norberg

(57) ABSTRACT

The invention relates to novel substrates and methods for staining live stem cells. The stain may be used to identify induced pluripotent stem cell colonies during the process of somatic cell reprogramming.

5 Claims, 6 Drawing Sheets

SUBSTRATES AND METHODS FOR STAINING LIVE STEM CELLS

CROSS-REFERENCE TO RELATED APPLICATIONS

This application is a national stage application filed under 35 U.S.C. §371 of PCT/2012/025123, filed Feb. 14, 2012, which claims priority to U.S. Provisional Patent Application No. 61/442,490, filed Feb. 14, 2011 and U.S. Provisional Patent Application No. 61/576,253, filed Dec. 15, 2011, all of which are commonly owned with the present application and the entire contents of both of which hereby expressly incorporated by reference in their entirety as though fully set forth herein.

TECHNICAL FIELD

The invention relates to novel substrates and methods for staining live cells. The stain may be used to identify specific cells based on a differential property, for example, identification of an induced pluripotent stem cell during the process of somatic cell reprogramming.

BACKGROUND

Embryonic stein cells (ESC) are derived from the inner cell mass of pre-implantation embryos, and have been recognized as the most pluripotent stem cell population. These cells are capable of unlimited, undifferentiated proliferation in vitro, and still maintain the capacity for differentiation into a wide variety of somatic and extra-embryonic tissues. Detection and identification of the cell type of interest is a critical step in the stem cell work flow. For example, during the process of somatic reprogramming, several colonies are obtained out of which only a few are truly pluripotent. Additionally stem cell populations are dynamic culture systems with the propensity for differentiation. For example, pluripotent stem cells such as ESC and induced pluripotent stem cells (iPSC) are characterized periodically to qualify their undifferentiated, pluripotent state. Current methods for detection/identification and characterization of pluripotent stem cells are primarily immunochemical staining methods, using antibodies against unique surface markers, which may be terminal and expensive.

Alternate methods include detection using alkaline phosphatase activity. Alkaline phosphatase is an enzyme in the blood, intestines, liver, and bone cells, and exists as membrane-bound isoforms of glycoproteins sharing a common protein structure but differing in carbohydrate content. These enzymes are most active at alkaline pH. Undifferentiated human pluripotent stem cells have been shown to express a very high level of alkaline phosphatase.

However, known substrates and methods for staining stem cells, including alkaline phosphatase staining methods, are generally terminal staining methods (i.e. toxic to the cells), and therefore are limiting as the stained colonies cannot be propagated further. Accordingly, there is a need in the industry for novel substrates and methods for staining stem cells using a solution that is both cell-permeable and nontoxic, and that specifically stains pluripotent stem cells without altering survival or stem cell characteristics. The invention described herein may, in various embodiments, solve some or all of these needs. The basic principle reported in this application can be extended to other cell types based on differential expression of a functional protein via delivery of the appropriate substrate that preserves the cells in their live condition.

SUMMARY

In accordance with various embodiments described herein, the inventors have discovered substrates and methods for staining cells, for e.g., undifferentiated stem cells, that are both cell-permeable and non-toxic. Due to their non-toxicity, these substrates and methods do not alter the integrity or characteristics of the stained cells. In fact, these novel substrates and methods preserve cellular integrity post-staining as the stained colonies survive and continue to proliferate without loss in viability, pluripotency, or differentiation capability. Due to the cell-permeability of the substrates, eventually, the substrate gets diluted out through routine cell culture maintenance, or through cell division. Therefore, the substrate eventually exits the cell without leaving any footprint, which is highly desirable for downstream clinical applications of an identified cell population.

The novel substrates and methods are, in at least some embodiments, amenable for both small-scale and large-scale culture systems, and can be used in multiple stages of the pluripotent stem cell workflow starting from iPSC colony detection to ESC/iPSC characterization.

During the process of reprogramming cells, several colonies may be obtained, only some of which are truly pluripotent. Current methods for determining such colonies are lengthy and tedious. For instance, antibody staining methods are expensive, time consuming and prone to microbial contamination, and may render an identified cell population useless for downstream applications. On the other hand, many of the novel substrates in this disclosure are small molecules, cell-permeable and non-toxic, and offer an attractive alternative to antibody staining methods.

The inventors have now discovered simpler methods where, for example, cell colonies obtained from a reprogramming process can be treated with the substrates disclosed herein, followed by a simple fluorescent readout.

The novel substrates and methods may allow one of skill in the art to identify a particular type of cell in colonies, which include cells other than stem cells and stem cells. This may be useful, for example, where the skilled artisan desires to identify and isolate iPSCs, tissue-specific stem cells, cells with certain properties, etc.

Accordingly, an embodiment of the invention is directed, in part, to a composition comprising a substrate capable of identifying a live stem cell of interest, wherein the substrate is cell permeable and is capable of being modified by the stem cell into a modified substrate, wherein the modified substrate is both permeable and detectable such that the live stem cell can be identified by detecting the presence of the modified substrate, and wherein the substrate and the modified substrate are non-toxic.

The compositions described in this disclosure are such wherein the live stem cell of interest is selected from the group consisting of an embryonic stem cell (ESC), an induced pluripotent stem cell (iPSC), a pluripotent cell, a progenitor cell, a reprogrammed cell, and a dedifferentiated cell.

The compositions described in this disclosure are such wherein the detecting is of a fluorescent signal.

The compositions described in this disclosure are such wherein the substrate is chosen from the group consisting of xanthene derivatives, coumarin derivatives, resorufin derivative, triphenylmethanes and dialkylacridinones.

The compositions described in this disclosure are such wherein the substrate may be a rosamine derivative.

The compositions described in this disclosure are such wherein the xanthene derivative is selected from the group consisting of fluorescein derivatives and rhodamine derivatives.

The compositions described in this disclosure are such wherein the fluorescein derivative is either a fluorescein monophosphate or a fluorescein diphosphate.

The compositions described in this disclosure are such wherein the fluorescein monophosphate may be chosen from compounds of formula Ia-b:

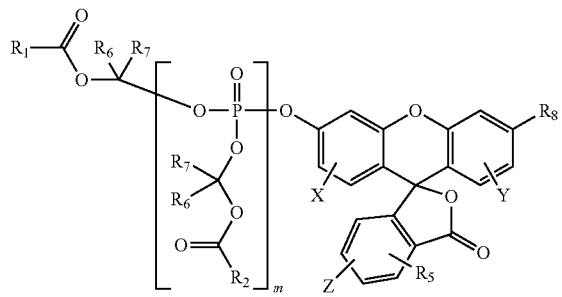

Ia

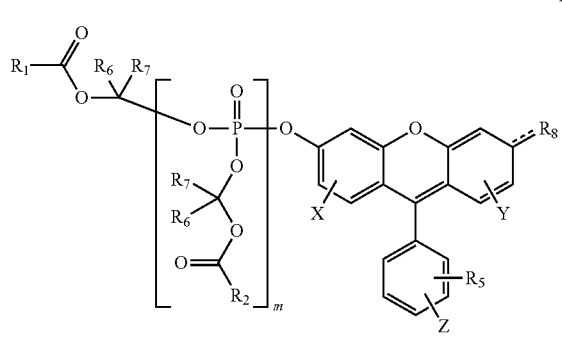

Ib where:
R1, R2, R3, R4, R6 and R7 are individually chosen from alkyl, aryl, aralkyl, heteroaryl, and heteroaralkyl;
X and Y are individually chosen from H, halogen, amino alkoxy, SH, SR, alkyl, aryl, aralkyl, heteroaryl, and heteroaralkyl;
Z and R5 are individually chosen from H, COOH, COOR, OH, amino, alkoxy, halogen, alkyl, aryl, aralkyl, heteroaryl, and heteroaralkyl;
R8 is chosen from NHCOR; and
m and n individually range from 1 to 3.

The composition described in this disclosure are such wherein the fluorescein diphosphate may be chosen from compounds of formula II:

X and Y are individually chosen from H, halogen, amino alkoxy, SH, SR, alkyl, aryl, aralkyl, heteroaryl, and heteroaralkyl;
Z and R5 are individually chosen from H, COOH, COOR, OH, amino, alkoxy, halogen, alkyl, aryl, aralkyl, heteroaryl, and heteroaralkyl;
R8 is chosen from NHCOR; and
m and n individually range from 1 to 3.

The composition described in this disclosure are such wherein the coumarin derivative is an umbelliferone derivative.

The composition described in this disclosure are such wherein the umbelliferone derivative may be chosen from compounds of formula VI:

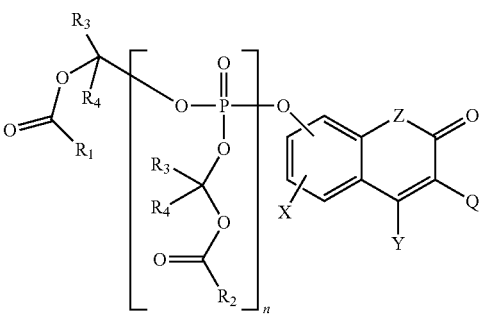

VI where:
R1, R2, R3, and R4 are individually chosen from alkyl, aryl, aralkyl, heteroaryl, and heteroaralkyl;
X is chosen from H, halogen, dihalo, trihalo, amino alkoxy, SH, SR, alkyl, aryl, aralkyl, heteroaryl, and heteroaralkyl;
Y is chosen from H, CN, alkyl, perfluoroalkyl, haloalkyl, aryl, aralkyl, heteroaryl, and carboxyalkyl;
Q is chosen from H, CN, alkyl, perfluoroalkyl, aryl, heteroaryl, a carboxamide, formyl, carboxy, carboxyalkyl, amino, alkyl-substituted amino;
Z is chosen from O, NH, and S; and
n ranges from 1 to 3.

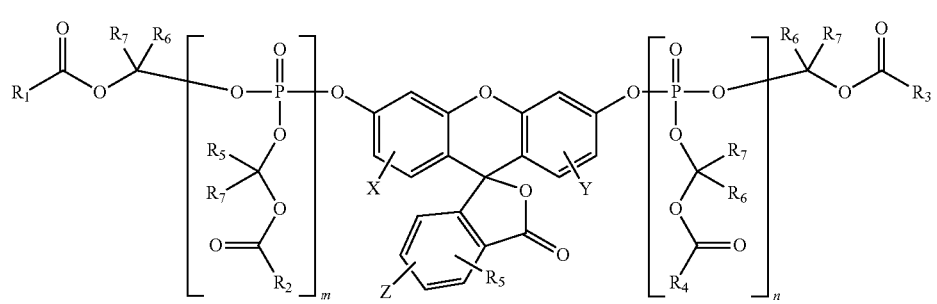

II where:
R1, R2, R3, R4, R6 and R7 are individually chosen from alkyl, aryl, aralkyl, heteroaryl, and heteroaralkyl;

The composition described in this disclosure are such wherein the compound is 6,8-difluoro-4-methylumbelliferyl phosphate (DiFMUP).

The compositions described in this disclosure are such wherein the triphenylmethane derivatives may be chosen from compounds of formula IV or V:

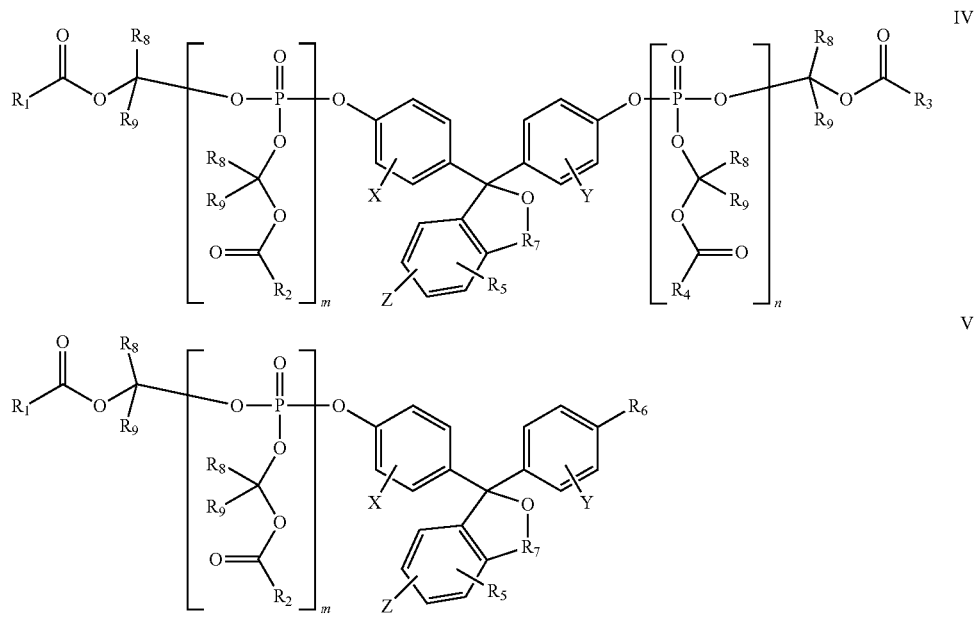

where:

$R_1$, $R_2$, $R_3$, $R_4$, $R_8$ and $R_9$ are individually chosen from alkyl, aryl, aralkyl, heteroaryl, and heteroaralkyl;

X and Y are individually chosen from H, halogen, amino alkoxy, SH, SR, alkyl, aryl, aralkyl, heteroaryl, and heteroaralkyl;

Z and $R_5$ are individually chosen from H, COOH, COOR, OH, amino, alkoxy, halogen, alkyl, aryl, aralkyl, heteroaryl, and heteroaralkyl;

$R_6$ is chosen from OR, NHCOR, and SR;

$R_7$ is chosen from C=O and S(O)$_2$; and m and n individually range from 1 to 3.

The compositions described in this disclosure are such wherein the substrate is reactive with enzymes chosen from acid or alkaline phosphatases.

The compositions described in this disclosure are such wherein the substrate is fluorescein diphosphate-AM ester of formula III:

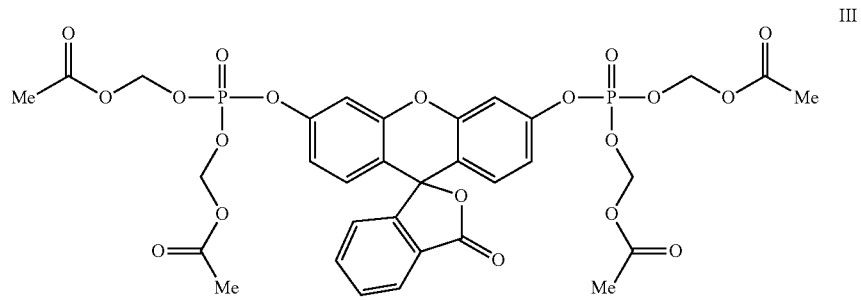 [SMILES: CC(=O)OCOP(=O)(OCOC(C)=O)Oc1ccc2c(c1)Oc1cc(OP(=O)(OCOC(C)=O)OCOC(C)=O)ccc1C21OC(=O)c2ccccc21]

The compositions described in this disclosure are such wherein the substrate is a resorufin derivative of formula VII or formula VIII:

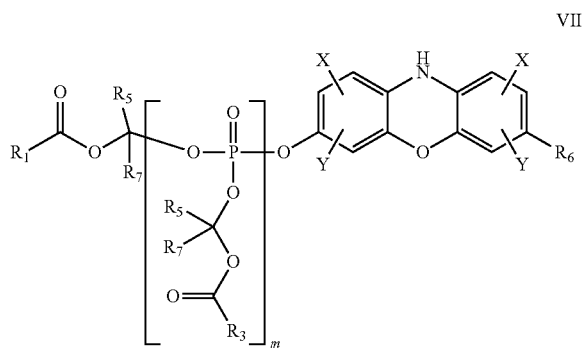

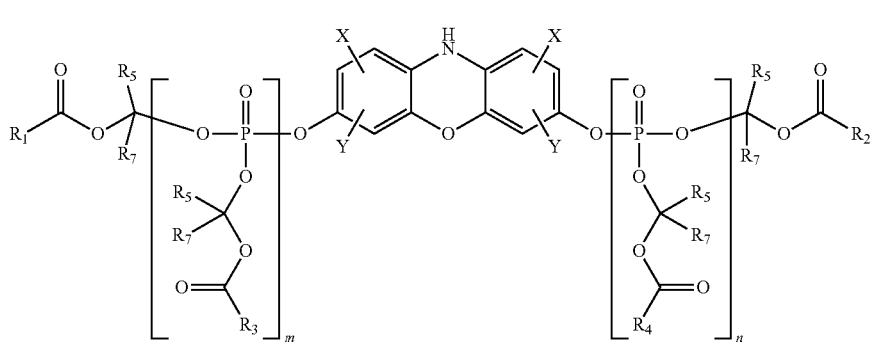

An embodiment of the invention is also directed, in part, to a method of identifying a live stem cell in a colony, said method comprising treating the colony with any of the compositions described above, wherein the composition comprises a substrate that is cell permeable and is capable of being modified by the stem cell into a modified substrate, wherein the modified substrate is both permeable and detectable such that the live stem cell can be identified by detecting the presence of the modified substrate, and wherein the substrate and the modified substrate are non-toxic.

The methods described in this disclosure are such, wherein the composition is a xanthene derivative.

The methods described in this disclosure are such, wherein the composition is reactive with an enzyme chosen from either an acid or an alkaline phosphatase.

The methods described in this disclosure are such, wherein the composition comprises a fluorescein diphosphate-AM ester.

An embodiment of the invention is also directed, in part, to a method of staining at least one stem cell in a cell culture, said method comprising treating the cell culture with any composition described above, wherein the composition is cell permeable, has a detectable signal and is non-toxic to said stem cell and specifically stains the stem cell.

The methods described in this disclosure are such, wherein the composition is a xanthene derivative.

The methods described in this disclosure are such, wherein the composition is reactive with an enzyme chosen from either an acid or an alkaline phosphatase.

The methods described in this disclosure are such, wherein the composition comprises a fluorescein diphosphate-AM ester.

An embodiment of the invention is also directed, in part, to a kit comprising any composition described above.

The kit described in this disclosure further comprises at least one vial comprising a cell.

The kit described in this disclosure is such wherein at least one vial comprises a stem cell.

The kit described in this disclosure comprises a compound of formula III:

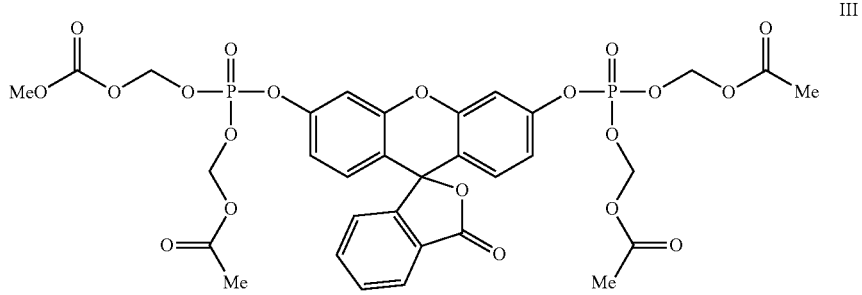 [SMILES: COC(=O)OCOP(=O)(OCOC(C)=O)Oc1ccc2c(c1)Oc1cc(OP(=O)(OCOC(C)=O)OCOC(C)=O)ccc1C21OC(=O)c2ccccc21]

An embodiment of the invention is also directed, in part, to a method of staining a live stem cell of interest, said method comprising treating said stem cell with any composition described above, wherein the composition comprises a substrate that is:
a. cell permeable;
b. non-toxic to the cell;

c. is processed to a modified substrate by the stem cell of interest,
wherein the modified substrate can be detected, and optionally, the modified substrate can diffuse out of the cell.

The method using any composition described above, is such wherein the live stem cell is selected from the group consisting of an embryonic stem cell (ESC), an induced pluripotent stem cell (iPSC), a pluripotent cell, a progenitor cell, a reprogrammed cell, and a dedifferentiated cell.

The method using any composition described above is such wherein the detecting is of a fluorescent signal.

The method using any composition described above is such wherein the substrate is modified by an enzyme specific to the live stem cell of interest.

The composition of any composition described above, is such wherein the substrate is modified by an enzyme specific to the live stem cell of interest.

The method using any composition described above, or any composition described above are such wherein the substrate is present in an effective amount for the detection of said live stem cell of interest.

The methods and/or the compositions are such wherein the effective amount of the substrate is 2-1000 mM; or wherein the effective amount of the substrate is 2-1000 µM.

The method using any composition described above are such wherein a further step of washing the live stem cell, or diluting the live stem cell with buffer and/or culture media, removes the modified substrate.

BRIEF DESCRIPTION OF THE FIGURES

The following figures, which are described below and which are incorporated in and constitute a part of the specification, illustrate exemplary embodiments of the invention and are not to be considered limiting of the scope of the invention.

DETAILED DESCRIPTION

Figure 1:
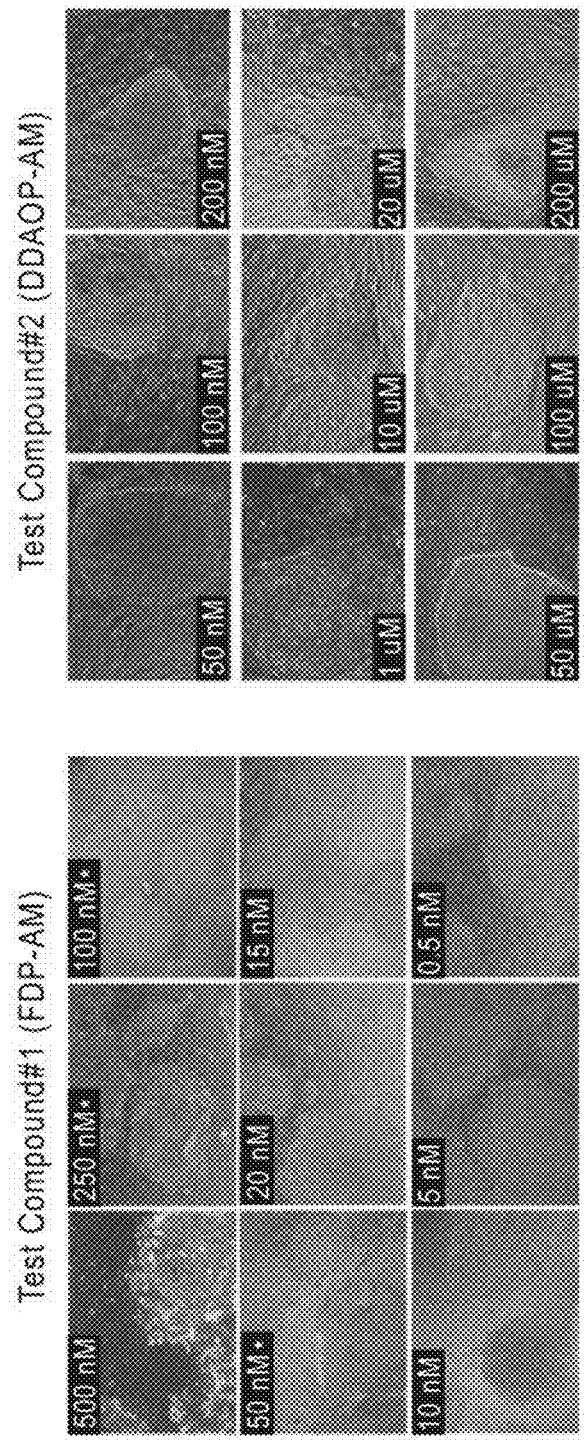
FIG. 1, left panel, shows fluorescence of FDP-AM in the nanomolecular range, and right panel shows fluorescence of DDAOP-AM in the micomolar range, as described in Example 1.

The disclosure relates to novel substrates and methods for staining live cells, for e.g., stem cells. In various embodiments, the substrates and/or methods are non-toxic to the cells. In further embodiments, the substrates are capable of diffusing in and out of the cells. In yet further embodiments, the substrates and methods do not disrupt the stained cell's integrity. It should, however, be understood that the invention, in its broadest sense, can be practiced without having one or more features of these aspects and embodiments.

DEFINITIONS

Stem Cell (SC): As used herein, the term "stem cell" may be any unspecialized, 'self-renewing' cell capable of developing into a variety of specialized cells and tissues. Self-renewing may mean that the cells have an ability to divide for indefinite periods (i.e., they do not undergo senescence, or can divide beyond twenty population doublings, which may be typical for a non-renewing cell) in appropriate culture conditions, while giving rise to a specialized cell under specified culture conditions. Self-renewal may be under tight control of specific molecular networks.

"Embryonic stem cells" (ESCs) are undifferentiated cells found in early embryos, and typically are derived from a group of cells called the inner cell mass, a part of the blastocyst. Embryonic stem cells are self-renewing and can form all specialized cell types found in the body (they are pluripotent). ESCs include ECSs of human origin (hESCs) and ESCs of non-human or animal origin. ESCs can typically be propagated, under appropriate conditions, without differentiation, due to their self-renewing properties.

"Pluripotent" or "multipotent" stem cells as used herein, have the ability to develop into more than one cell type of the body. However, pluripotent cells generally cannot form "extra-embryonic" tissues such as the amnion, chorion, and other components of the placenta. Pluripotency may be demonstrated by providing evidence of stable developmental potential even after prolonged culture, and can form derivatives of all three embryonic germ layers from the progeny of a single cell, and by showing the ability to generate a teratoma after injection into an immunosuppressed mouse. Pluripotency may be under tight control by specific molecular networks.

A "progenitor cell" may be an early descendant of a stem cell that can differentiate, and have a capacity to differentiate into a specific type of cell. Progenitor cells are more differentiated than stem cells. Sometimes, the terms "stem cell" and "progenitor cell" may be found to be equated herein.

"Adult stem cells" may be obtained from, among other sources, blood, bone marrow, brain, pancreas, skin and the fat of adult bodies. Adult stem cells can renew themselves and differentiate to give rise to a limited repertoire of specialized cell types, usually of the tissue type from which it originated. In certain cases, some adult stem cells, under certain growth conditions, can give rise to cell types associated with other tissues (multipotent).

"Somatic stem cells" are non-embryonic stem cells that are not derived from gametes (egg or sperm cells). These somatic stem cells may be of fetal, neonatal, juvenile or adult origin.

Reprogramming may be done for any reason, for example, to achieve a less differentiated status in certain instances, or a more differentiated status, or for directed differentiation. That is, reprogramming could be done to alter the differentiation capacity of a cell. For instance, methods of the invention may achieve a more stem-like status from a more differentiated stage; or a more non-cancerous state from a cancer state, or disease-free state from a diseased cell, etc. In certain instances, "reprogramming" may use one or more stem cell marker genes like Oct4 (also termed Oct-3 or Oct3/4), Sox2, c-Myc, Klf4, Oct3/4, Nanog, SSEA1 (Stage Specific Embryonic Antigens), TRA1-80, etc. to reprogram a somatic or an adult cell towards a less differentiated status.

A number of stem cell specific developmental genes are discussed in this invention. Stem cell markers include, but are not limited to, genes such as Oct4 (also termed Oct-3 or Oct3/4), Sox2, c-Myc and Klf4; Oct3/4, Nanog, SSEA1 (Stage Specific Embryonic Antigens), TRA1-80, etc. Unique expression markers are also used to characterize various stem cell populations such as CD34, CD133, ABCG2, Sca-1, etc. for hematopoietic stem cells; STRO-1, etc. for mesenchymal/stromal stem cells; nestin, PSA-NCAM, p75 neurotrophin R(NTR), etc. for neural stem cells.

Substrates for Staining Cells

In one embodiment, the disclosure relates to substrates or stains that are useful for staining cells, for e.g., stem cells. In various embodiments, the substrates are not toxic to the stem cells. In other embodiments, the substrates preserve the integrity and/or the viability of the cell, and may be referred to as a live stain. In other embodiments, the substrates can enter the stem cells (are cell permable) and are substrates for differentially expressed cellular molecules, such as an enzyme. In a further embodiment, the substrate may be modified by one or more differentially expressed cellular molecule(s), such as enzyme(s), to expose an identifier moiety on the substrate, such as a fluorescent moiety, resulting in a measurable signal. In yet a further embodiment, the measurable signal varies between cells that either has the differentially expressed cellular molecule or does not have, or have lower amounts of, the differentially expressed cellular molecule (for e.g., an enzyme). In another further embodiment, the modified substrate within the cell is also permeable and can leave the cell after certain number of passages, or by dilution with cell medium/buffer, or by washing the cells, etc. As a further application of this embodiment, if the modified substrate could be identified with a signal such as a fluorescent signal, then over time, the measurable signal (fluorescence) would diminish as the modified substrate is diluted from the cell and leaves no trace or footprint on the isolated cell or clone.

Therefore, the differential signal can help to identify, and/ or isolate certain types of cells from cells that do not/express lower amounts of the differentially expressed cellular molecule, and can eventually leave the cell without leaving a footprint, which is preferable for downstream clinical applications. Substrates useful herein may, therefore, offer an alternative for live staining of stem cells, identification and propagation of the live stained stem cells for downstream applications, including clinical applications. Substrates useful herein may further allow for a simplified method of staining, relative to known methods.

In one embodiment presented herein, the substrates and methods of the invention are directed to the differentially expressed cellular molecule, the alkaline phosphatase enzyme that is specifically expressed in pluripotent stem cells such as ESCs and iPSCs, and further, also in some specialized tissue cells such as differentiating osteoblasts. Accordingly, parent substrates have been constructed that are cell permeant, non-toxic and either non-fluorescent or non-chromogenic (or both) (see FIG. 9). In an exemplary embodiment, a parent enzyme substrate that is cell permeant, non-toxic and non-fluorescent, upon entry into a cell of interest, gets cleaved by the cell's ubiquitous cellular esterases, into an intermediate, non-permeable substrate for another 'cell of interest-specific' enzyme, for e.g., a pluripotent stem cell-specific alkaline phosphatase. This results in the generation of a fluorescent compound or a chromogenic compound that can be detected by a suitable means, and additionally, the resultant compound is non-toxic and cell permeable, and hence eventually can leach out of the cell after cell culturing. In an alternate embodiment, the parent substrate in cleaved in one-step to the final product for cell detection (general platform). The basic principle of a cell permant substrate being converted to non-toxic, fluorescent and/or chromogenic compounds for cell-specific detection, that optionally may be permeable, and can be extended for the detection of any cell type with a cell-specific functional protein (for e.g., cell-specific enzymes, a cell- or tissue-specific metabolic process, that is unique to a particular cell type such as an unique transporter, or a synthetic or degradation pathway, etc.), thus permitting cell identification during proliferation without loss of its viability or cell-specific properties.

Exemplary substrates that may be useful include, but are not limited to, substrates that can be cleaved by phosphatases, including acid and alkaline phosphatases, and derivatives thereof. Such substrates may comprise moieties enabling detection, such as, fluorescent moieties (including Qdot® nanocrystals), chromogenic moieties, moieties that are pH sensitive, etc. Examples of substrates include, but are not limited to, xanthene derivatives, coumarin derivatives, resorufin derivatives, dyes derived from the triphenylmethane class, dialkylacridinones, etc. In some exemplary embodiments, substrates include xanthene derivatives including, but are not limited to, fluorescein monophosphate derivatives, fluorescein diphosphate derivatives, rhodamine derivatives, etc. In exemplary embodiments, the methods disclosed herein use xanthene derivatives selected from the group consisting of fluorescein derivatives and rhodamine derivatives, excluding rosamine derivatives. In other exemplary embodiments, the methods disclosed herein use xanthene derivatives that include certain types of rosamine derivatives, except for a rosamine of the structure X (shown below):

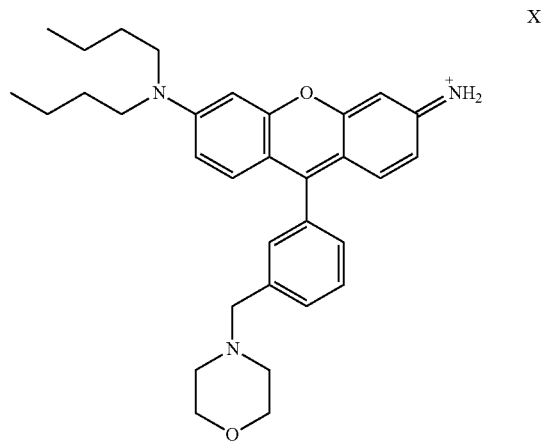 [SMILES: CCCCN(CCCC)c1ccc2c(-c3cccc(CN4CCOCC4)c3)c3ccc(=N)cc-3oc2c1]

In other exemplary embodiments, substrates may include coumarin derivatives including, but are not limited to, derivatives of umbelliferones, such as fluorinated umbelliferones, like DiFMUP (6,8-difluoro-4-methylumbelliferyl phosphate), etc. In other exemplary embodiments, substrates include resorufin derivatives. In further exemplary embodiments, substrates may include, but are not limited to, dyes from the triphenylmethane class like bromocresol, phenolphthalein, etc; or, dialkylacridinones, such as 7-hydroxy-9H-(1,3-dichloro-9,9-dimethylacridin-2-one) (DDAO), etc.

Exemplary fluorescein monophosphate derivatives may be chosen from compounds of formula Ia-b, and exemplary fluorescein diphosphate derivatives may be chosen from compounds of formula II:

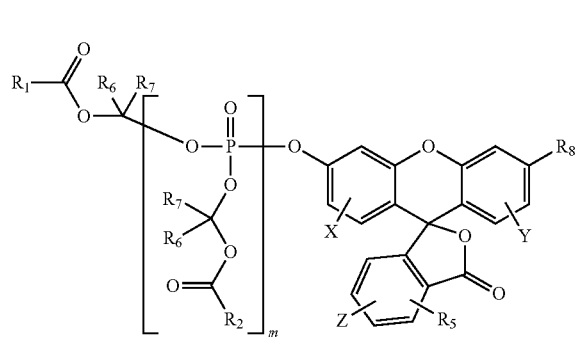

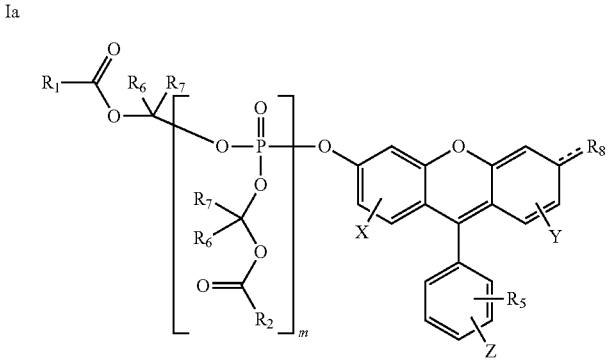

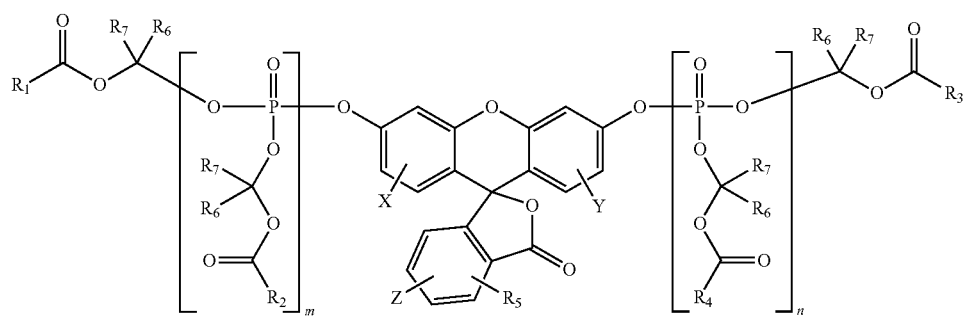

where:
R1, R2, R3, R4, R6 and R7 are individually chosen from alkyl, aryl, aralkyl, heteroaryl, and heteroaralkyl;
X and Y are individually chosen from H, halogen, amino alkoxy, SH, SR, alkyl, aryl, aralkyl, heteroaryl, and heteroaralkyl;
Z and R5 are individually chosen from H, COOH, COOR, OH, amino, alkoxy, halogen, alkyl, aryl, aralkyl, heteroaryl, and heteroaralkyl;
R8 is chosen from NHCOR; and
m and n individually range from 1 to 3.

By way of example only, fluorescein diphosphate-AM esters of formula III may be used:

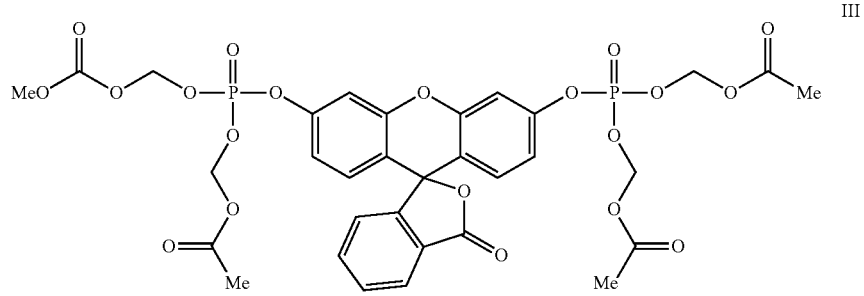 [SMILES: COC(=O)OCOP(=O)(OCOC(C)=O)Oc1ccc2c(c1)Oc1cc(OP(=O)(OCOC(C)=O)OCOC(C)=O)ccc1C21OC(=O)c2ccccc21]

Exemplary dyes from the class of triphenylmethanes may be chosen from compounds of the following formulae IV and V:

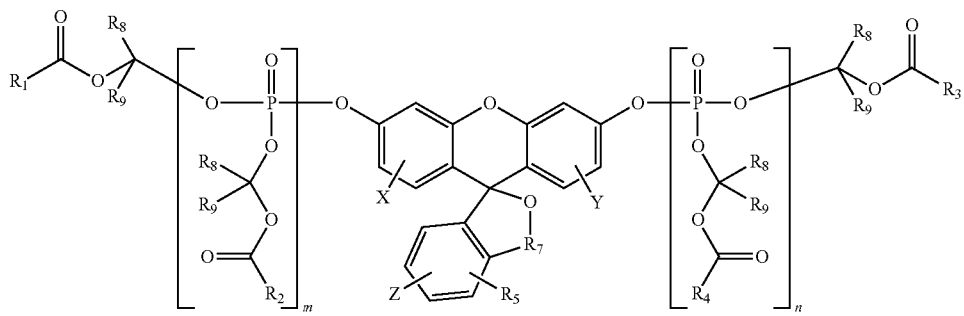

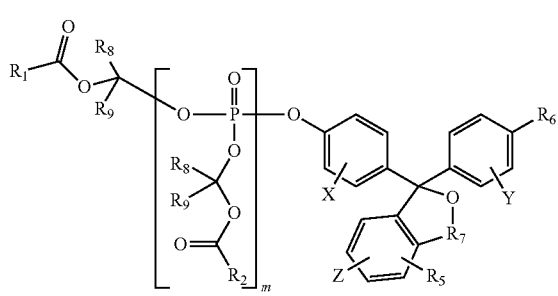

where:

R1, R2, R3, R4, R8 and R9 are individually chosen from alkyl, aryl, aralkyl, heteroaryl, and heteroaralkyl;

X and Y are individually chosen from H, halogen, amino alkoxy, SH, SR, alkyl, aryl, aralkyl, heteroaryl, and heteroaralkyl;

Z and R5 are individually chosen from H, COOH, COOR, OH, amino, alkoxy, halogen, alkyl, aryl, aralkyl, heteroaryl, and heteroaralkyl;

R6 is chosen from OR, NHCOR, and SR;

R7 is chosen from C=O and $S(O)_2$; and m and n individually range from 1 to 3.

By way of example only, bromocresol derivatives may be used, such as bromocresol purple and bromocresol green.

Exemplary derivatives of umbelliferone compounds may be chosen from compounds of formula VI:

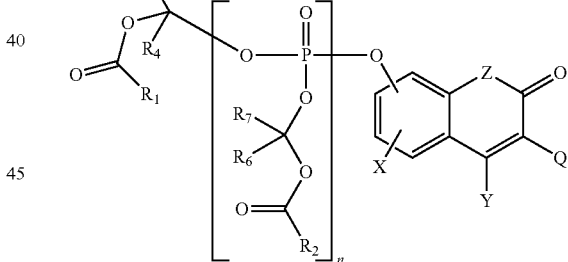

where:

R1, R2, R3, and R4 are individually chosen from alkyl, aryl, aralkyl, heteroaryl, and heteroaralkyl;

X is chosen from H, halogen, dihalo, trihalo, amino alkoxy, SH, SR, alkyl, aryl, aralkyl, heteroaryl, and heteroaralkyl;

Y is chosen from H, CN, alkyl, perfluoroalkyl, haloalkyl, aryl, aralkyl, heteroaryl, and carboxyalkyl;

Q is chosen from H, CN, alkyl, perfluoroalkyl, aryl, heteroaryl, a carboxamide, formyl, carboxy, carboxyalkyl, amino, alkyl-substituted amino;

Z is chosen from O, NH, and S; and n ranges from 1 to 3.

By way of example only, 6,8-difluoro-4-methylumbelliferyl phosphate (DiFMUP) may be used.

Exemplary resorufin derivatives may be chosen from resorufin monophosphate compounds of formula VII, and resorufin diphosphate compounds of formula VIII:

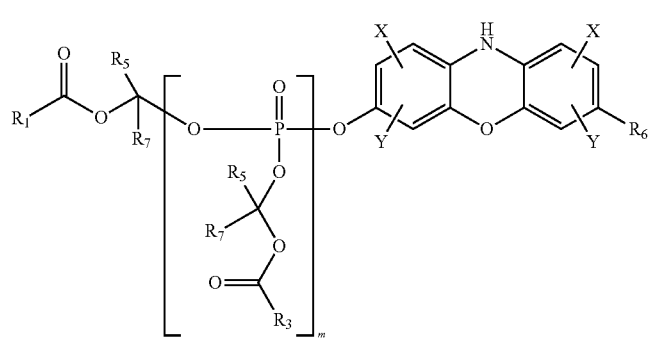

VII

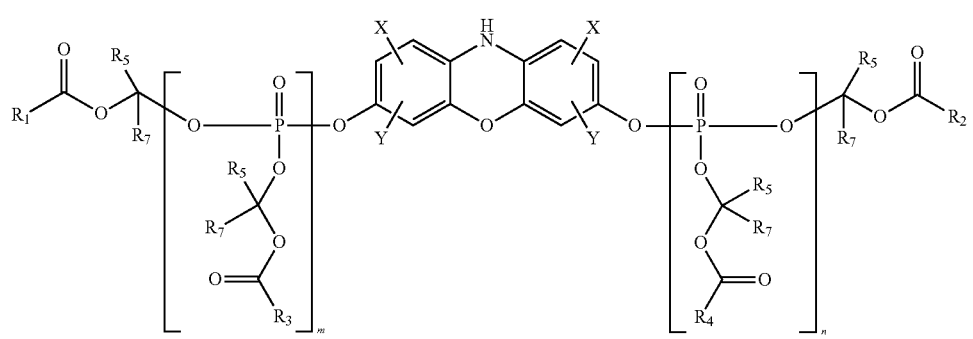

VIII where:

R1, R2, R3, R4, and R7 are individually chosen from alkyl, aryl, aralkyl, heteroaryl, and heteroaralkyl;

X and Y are individually chosen from H, halogen, amino alkoxy, SH, SR, alkyl, aryl, aralkyl, heteroaryl, and heteroaralkyl;

Z and R5 are individually chosen from H, COOH, COOR, OH, amino, alkoxy, halogen, alkyl, aryl, aralkyl, heteroaryl, and heteroaralkyl;

R6 is chosen from OR, NHCOR, and SR; and m and n individually range from 1 to 3.

By way of example only, compounds of formula VII may be chosen from compounds of formulae VIIa and VIIb:

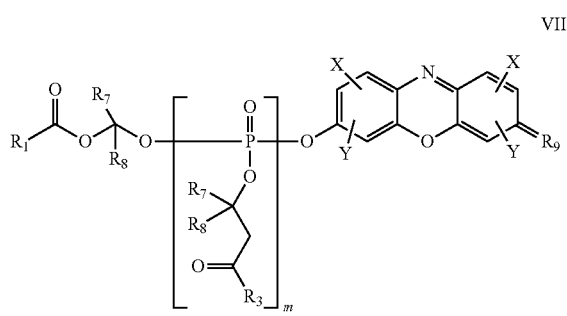

VIIa

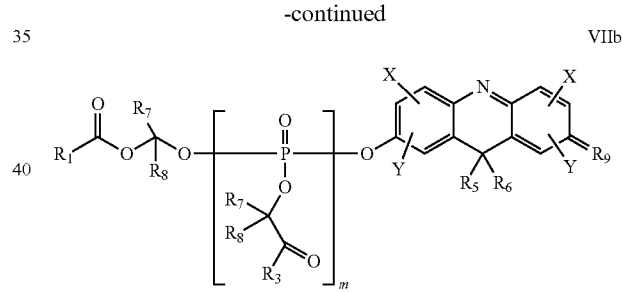

VIIb where:

R1 and R3 are individually chosen from alkyl, branched alkyl, substituted alkyl, aryl and heteroaryl;

R5 and R6 are individually chosen from alkyl, substituted alkyl and an alkyl that can form an alicyclic ring of 4-8 members;

R7 and R8 are individually chosen from alkyl, aryl, aralkyl, heteroaryl and heteroaralkyl;

X and Y are individually chosen from H, halogen, amino, alkoxy, SH, SR, alkyl, aryl, aralkyl, heteroaryl and heteroaralkyl;

R9 is chosen from O, NR2 (where R is chosen from hydrogen, alkyl, substituted alkyl, aryl and heteroaryl) and S; and m ranges from 1 to 3.

As indicated above, it may also be possible to use DDAO substrates, including, for example, compounds of formulae IXa and IXb:

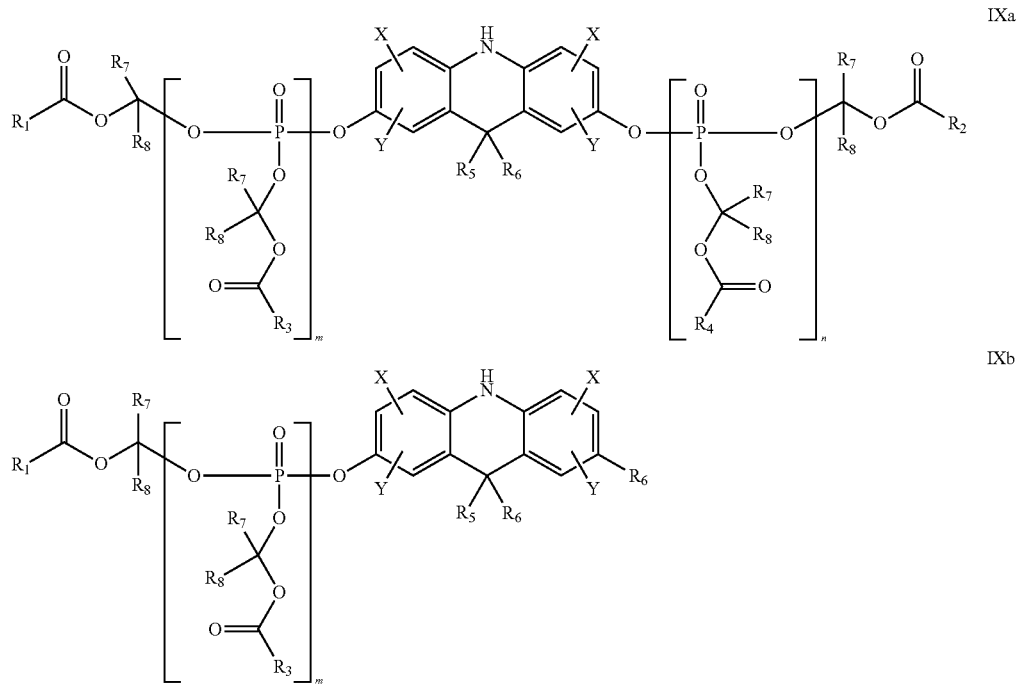

where:

R1, R2, R3, R4, R7, and R8 are individually chosen from alkyl, aryl, aralkyl, heteroaryl, and heteroaralkyl;

X and Y are individually chosen from H, halogen, amino alkoxy, SH, SR, alkyl, aryl, aralkyl, heteroaryl, and heteroaralkyl;

Z and R5 are individually chosen from H, COOH, COOR, OH, amino, alkoxy, halogen, alkyl, aryl, aralkyl, heteroaryl, and heteroaralkyl;

R6 is chosen from OR, NHCOR, and SR; and m and n individually range from 1 to 3.

By way of example only, DDAO phosphate-AM esters of formula X may be used:

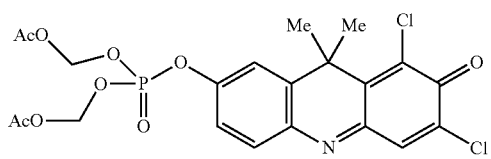

As used herein, the term "derivative" is meant to include compounds derived from the specific compound or class of compounds, and analogs of the compound.

Additional cell markers, enzymes or surface antigens for which useful, live staining substrates can be made include somatic cell markers as well as stem cell markers; for e.g., they include, but are not limited to, other tissue stem cell-specific alkaline phosphatases such as placental alkaline phosphatase, ALDH1 (aldehyde dehydrogenase), DNMT3b (de novo DNA methylatransferase), ABCG2 (ATP-binding cassette superfamily G member 2), other stem cell surface antigens such as CD133/SSEA4/TRA181, etc., neural stem cell markers such as PSA-NCAM, p75 NTR (neurotropin), etc., NAAG synthetase in oligodendrocytes, Gamma GST, CD44-truncated cancer variant, CEA antigen, stress kinases in $O_2$ deprived cells, acid phosphatases in prostate cells, etc. One of skill in the art, reviewing the disclosure, will appreciate that many substrates may be useful in the methods described herein, without departing from the scope of the invention. It is within the knowledge of those of ordinary skill, using routine experimentation, to prepare a substrate having the disclosed unique activity to a particular cell type, e.g. to prepare substrates useful for diffusing in and out of cells while being non-toxic, yet useful for staining.

Methods for Staining Cells

The disclosure further relates to methods of staining cells, such as, for example, live iPSCs, and methods of identifying such stained cells over background unstained cells. In various embodiments, the methods include treating cell colonies with the substrates disclosed herein, followed by a simple fluorescent readout. In at least certain embodiments, the methods disclosed herein do not affect cell or colony viability, pluripotency, and/or differentiation capability. In further embodiments, the substrate may diffuse out of the cell, post-staining; for example, after repeated washing of the cells with buffer, or additional of new medium to the cell culture, etc. In that case, cells may optionally be restained at a later time, if desired.

In various methods of the disclosure, exposure of cells to a substrate at a particular range of fluorescence may occur for a particular period of time, in a particular medium. By way of example only, exposure may be in the range of about 50 nm to about 200 μm. The substrate may, for example, be exposed from about 5 minutes to about 1 hour. In addition, media that may be used in the methods described herein are those that are known in the art, such as, for example, DMEM (Dulbecco's Modified Eagle's Medium), or optimal basal media used to culture cells of interest. One of skill in the art, however, will appreciate that the range of fluorescence, the time of exposure, the media chosen, and other variables will be chosen based on, for example, the particular substrate chosen, particular cell type, etc.

In various embodiments of the disclosure, since the cell-permeable substrate is nontoxic to the cells, positively stained cells can be further propagated for downstream applications. These properties therefore impart superior results relative to current methods of alkaline phosphatase staining that are terminal and do not preserve cellular integrity post-staining. It further addresses a key customer need for a reliable, fast and easy pluripotent identification/detection and characterization tool that can be used alone or in combination with other pluripotent markers.

Substrates and Methods for Identifying a Pluripotent Stem Cell (PSC)

The inventive substrates disclosed herein, that may be both cell-permeable and non-toxic, and the methods for using them, may be useful in identifying cells with specific properties, for e.g., cells that express (or do not express) a certain protein or enzyme. A desirable and preferred property of the novel substrates and methods is that, they preserve cellular integrity post-staining, i.e. the stained colonies can survive and continue to proliferate without loss in their viability, pluripotency, or differentiation capability.

In various embodiments described in this disclosure, the substrates and methods of the invention are useful for staining, identification and monitoring differentiation of a variety of cells in culture. After identification, the substrates and methods may be useful to enrich certain desired cell types. For example, a culture of undifferentiated cell may include lesser differentiated cells. In some embodiments, the undifferentiated or lesser differentiated cell may be a stem cell of any one or more of the following types: pluripotent stem cells (PSC), induced pluripotent stem cells (iPSC), embryonic stem cells (ESC), progenitor cells, multipotent cells, totipotent cells, tissue-specific stem cells, etc. In some embodiments, the differentiated cell may have a higher expression of a specific property (for e.g., higher metabolic activity or protein marker expression) over the undifferentiated cell. An example of this would be higher enzyme expression of alkaline phosphatase in differentiating osteocyte/blast derived cells over undifferentiated adipose derived mesenchymal stem cells (AdSCs). In certain embodiments, besides enzyme expression, it could be other cell markers which include, but are not limited to, other tissue stem cell-specific alkaline phosphatases such as placental alkaline phosphatase, ALDH1 (aldehyde dehydrogenase), DNMT3b (de novo DNA methylatransferase), ABCG2 (ATP-binding cassette superfamily G member 2), other stem cell surface antigens such as CD133/SSEA4/TRA181, etc., neural stem cell markers such as PSA-NCAM, p75 NTR (neurotropin), etc., NAAG synthetase in oligodendrocytes, Gamma GST, CD44-truncated cancer variant, CEA antigen, stress kinases in $O_2$ deprived cells, acid phosphatases in prostate cells, etc, which can be identified over background staining of cells not expressing a certain marker. Therefore, one of skill in the art will appreciate that, the substrates and methods of the invention may be useful in identifying cells with specific properties, for e.g., cells that express (or do not express) a certain protein or enzyme or metabolic pathway, over other cells that do not possess that specific property, and this in turn would be useful in identifying, and further isolating and characterizing, certain cell types over other cells, in a mixture.

An exemplary embodiment would be, during the process of reprogramming cells, several colonies may be obtained, but only some of which may be truly pluripotent. Therefore, in one embodiment, the novel substrates and methods described in this invention may be useful in staining and identifying pluripotent cells over other cells having a more differentiated status. In another embodiment, the novel substrates and methods may be useful to monitor the expansion of clonal and/or cell cultures derived from ESCs and iPSCs. In a further embodiment, the novel substrates and methods may be useful in identifying and/or isolating cells with certain properties with desired properties, for example; visual identification of emerging iPSC clones during reprogramming; confirmation of established iPSC colonies; characterization of pluripotent stem cells, for e.g., ESCs versus iPSCs; tissue-specific stem cells, etc. Therefore, the novel substrates and methods may also be useful in ESC/iPSC characterization. Hence, one of skill in the art may be able to identify and/or isolating a particular type of cell from colonies, using the novel substrates and methods disclosed here, which include cells other than stem cells, for example, based on their inability to be stained.

In some preferred embodiments, the substrates and methods disclosed herein may be particularly useful in staining and identifying plants, fungi, animals, embryos, vertebrates, invertebrates, etc. over other cells in a mixture of cells. In certain preferred embodiments, the substrates and methods disclosed herein may be particularly useful in staining and identifying cell types representative of the three germ layers of development (for e.g., ectoderm, mesoderm, endoderm, or any classification that is well-characterized in developmental biology), and therefore is applicable in whole organism staining. In a further aspect, the substrates and methods disclosed herein may be particularly useful in staining and identifying cell types in whole tissues, sections of tissues, whole organs, sections of organs, whole organism staining; for example, including but not restricted to, various organisms and species of; for example, *Planaria, Caenorhabditis, Drosophila*, etc. Therefore, the substrates and methods could be useful to stain the cells of tissue sections, organs, parts of tissues or organs, or entire organisms including embryos.

In a preferred embodiment, the stains or substrates and methods of the invention may be used in a high-throughput (HTS) format to screen and identify undifferentiated versus differentiated cells in a plurality of cultures, under a variety of environmental conditions. In one exemplary aspect of this embodiment, the stains or substrates and methods of the invention may be used in a high-throughput (HTS) format to screen and identify osteoblasts versus MSCs in a plurality of cultures, under a variety of environmental conditions. Therefore, the substrates and methods of the invention can be used to identify inducers of bone formation. Enriched osteoblast cell cultures would be useful for downstream applications, including but not limited to applications such as 3D bone reconstruction, cell therapy, etc.

In another preferred embodiment, the stains or substrates and methods of the invention may be used in a high-throughput (HTS) format to screen, identify and monitor undifferentiated versus differentiated cells in various cultures, for example, in corneal cultures, such as in differentiating between limbal and corneal endothelium. In other preferred embodiments, the stains or substrates and methods of the invention may be used screen, identify and monitor undifferentiated versus differentiated cells in transgenic cell cultures, transgenic animals, cell cultures for transplantation, etc.

Therefore, in almost every embodiment described above, the methods of this invention are useful to identify any stained cell with a higher signal (for e.g., a pluripotent stem cell) over a control cell (sometimes referred to as a negative control), or a background stained cells (for e.g., a non-stem cell). In certain embodiments, the higher signal may be expressed in % staining of the cells above control staining, which may be at least about 2% to at least about 90%, at least about 2% to at least about 80%, at east about 2% to at least about 70%, at least about 2% to at least about 60%, at least about 2% to at least about 50%, at least about 2% to at least about 40%, at least about 2% to at least about 30%, at least about 2% to at least about 20%, at least about 2% to at least about 10%, at least about 10% to at least about 90%, at least about 10% to at least about 80%, at least about 10% to at least about 70%, at least about 10% to at least about 60%, at least about 10% to at least about 50%, at least about 10% to at least about 40%, at least about 10% to at least about 30%, at least about 20% to at least about 30%, at least about 20% to at least about 50%, at least about 20% to at least about 70%, etc., more than the staining of a background cell, or control cell, or cells in a control dish or plate stained with the same stain. In one embodiment, the effective concentration is a concentration when a live stem cell can be detected as compared to a control cell, or a non-stem cell. The effective concentration can readily be determined by one of skill in the art without undue experimentation.

Following identification and selection of a live stem cell by a suitable means (for example, by using the E-Z passage tool by Life Technologies, Inc.), the stem cells may be further expanded, or cultivated, and may be useful for downstream applications, including research, bioproduction of molecules of clinical interest, or for clinical applications.

In certain embodiments, the stains defined in this disclosure stain and/or identify stem cells, for e.g., ESCs, and/or iPSCs, better than other existing dyes in the market. For example, the substrates or stains described here stained stem cells and/or identified stem cells over control cells or background staining, or identified emerging iPSC cells/clones after reprogramming, at least about 2% to at least about 90%, at least about 2% to at least about 80%, at least about 2% to at least about 70%, at least about 2% to at least about 60%, at least about 2% to at least about 50%, at least about 2% to at least about 40%, at least about 2% to at least about 30%, at least about 2% to at least about 20%, at least about 2% to at least about 10%, at least about 10% to at least about 90%, at least about 10% to at least about 80%, at least about 10% to at least about 70%, at least about 10% to at least about 60%, at least about 10% to at least about 50%, at least about 10% to at least about 40%, at least, about 10% to at least, about 30%, at least about 20% to at least about 30%, at east about 20% to at east about 50%, at least about 20% to at least about 70%, etc., better than a control stain or substrate, or other stains in the market. Percent comparisons of staining and/or identification can readily be determined by one of skill in the art without undue experimentation.

In another embodiment, the stains defined in this disclosure stained and preserved cell viability, for e.g., ESCs, and/or iPSCs cell viability, better than other stains in the market. For example, the stains described here stained stem cells and/or preserved stem cell viability, or preserved emerging iPSC cells/clones viability after reprogramming, at least about 2% to at least about 90%, at east about 2% to at least about 80%, at east about 2% to at least about 70%, at east about 2% to at least about 60%, at least about 2% to at least about 50%, at least about 2% to at least about 40%, at least about 2% to at least about 30%, at least about 2% to at least about 20%, at least about 2% to at least about 10%, at least about 10% to at least about 90%, at least about 10% to at east about 80%, at least about 10% to at east about 70%, at least about 10% to at least about 60%, at least about 10% to at least about 50%, at least about 10% to at least about 40%, at least about 10% to at least about 30%, at least about 20% to at least about 30%, at least about 20% to at least about 50%, at least about 20% to at least about 70%, etc., better than control substrates or stains, or other stains in the market. Percent comparisons of viability can readily be determined by one of skill in the art without undue experimentation.

In yet another embodiment, the stains defined in this disclosure stained and maintained a normal karyotype of the expanded stem cell clones, for e.g., ESCs, and/or iPSCs, after staining, better than a control substrate or stain, 2% to at least about 80%, at least about 2% to at least about 70%, at least about 2,% to at least about 60%, at least about 2% to at least about 50%, at least about 2% to at least about 40%, at least about 2% to at least about 30%, at least about 2% to at least about 20%, at least about 2% to at least about 10%, at least about 10% to at least, about 90%, at east about 10% to at least about 80%, at east about 10% to at east about 70%, at least about 10% to at least about 60%, at least about 10% to at least about 50%, at least about 10% to at least about 40%, at least about 10% to at least about 30%, at least about 20% to at least about 30%, at least about 20% 10 at least about 50%, at least about 20% to at least about 70%, etc., better than stains available in the market. For example, the stains described here stained and maintained a normal karyotype of the expanded stem cell clones, or preserved normal karyotype of emerging iPSC after reprogramming. Percent comparisons of maintenance of karyotype after reprogramming, compared to a control substrate can readily be determined by one of skill in the art without undue experimentation.

In a further embodiment, the stains defined in this disclosure stained, maintained a normal karyotype of the expanded stem cell clones, and further expressed other pluripotent markers in some or all stem cell clones, better than other stains in the market, for instance, at least about 2% to at least about 90%, at least about 2% to at least about 80%, at least about 2% to at least about 70%, at least about 2% to at least about 60%, at least about 2% to at least about 50%, at least about 2% to at least about 40%, at least about 2% to at least about 30%, at least about 2% to at east about 20%, at least about 2% to at east about 10%, at least about 10% to at least about 90%, at least about 10% to at least about 80%, at least about 10% to at least about 70%, at least about 10% to at least about 60%, at least about 10% to at least about 50%, at least about 10% to at least about 40%, at least about 10% to at least about 30%, at least about 20% to at least about 30%, at least about 20% to at least about 50%, at least about 20% to at least about 70%, etc., better than stains available in the market. For example, the stains described here stained, maintained a normal karyotype of the expanded stem cell clones, and further expressed other pluripotent markers in some or all stem cell clones in emerging iPSC after reprogramming. Percent expression of pluripotent stem cell markers compared to control substrates can readily be determined by one of skill in the art without undue experimentation.

The final effective concentration of a dye, that was non-toxic and/or cell permeable, on cells, was either in the nanomolar range for certain dyes, for e.g., 5-1000 nM, or, were in the micromolar range for other dyes, for e.g., 5-1000 μM. For instance, the final effective concentration of a dye substrate on cells could be, at least about 5-1000 nM, at least about 5-800 nM, at least about 5-600 nM, at least about 5-500 nM, at least about 5-400 nM, at least about 5-300 nM, at least about 5-200 nM, at least about 5-100 nM, at least about 5-50 nM, at least about 50-800 nM, at least about 50-600 nM, at least about 50-500 nM, at least about 50-400 nM, at least about 50-300 nM, at least about 50-200 nM, at least about 50-100 nM, at least about 50-80 nM, etc. For another dye, the final effective concentration could be, at least about 5-1000 μM, at least about 5-800 μM, at least about 5-600 μM, at least about 5-500 μM, at least about 5-400 μM, at least about 5-300 μM, at least about 5-200 μM, at least about 5-100 μM, at least about 5-50 μM, at least about 50-800 μM, at least about 50-600 μM, at least about 50-500 μM, at least about 50-400

μM, at least about 50-300 μM, at least about 50-200 μM, at least about 50-100 μM, at least about 50-80 μM, etc. Preferred final effective concentrations which were non-toxic and/or cell permeable on the cells were, for e.g., 50-200 nM for certain dyes, or, 50-200 μM for other dyes. The effective concentration can be readily determined by one of skill in the art without undue experimentation.

In one aspect of the invention, the various substrates and methods described herein may be useful for preparing kits that comprises at least one of the substrates described herein.

In further embodiments of the disclosure, it is possible to use the substrates and methods described herein in combination with other known methods of PSC detection, such as, for example, live staining with surface antibodies, such as SSEA4, TRA-160, TRA-181, CD24, E-adherin, CD133 and other surface markers associated with pluripotent stem.

Although the disclosure relates to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

The use of the terms "the," "a," "an," or other singular terms, is meant to include plural embodiments as well, and vice versa. In addition, it should be understood that all numbers herein are modified by "about," whether or not so stated.

Moreover, it should be understood that various features and/or characteristics of differing embodiments herein may be combined with one another. It is therefore to be understood that numerous modifications may be made to the illustrative embodiments without departing from the scope of the invention. For example, in addition to positive identification and selection of a target cell, as exemplified by the alkaline phosphatase substrate described herein, substrates that may not be 'cleaved' by any cellular enzyme or cellular apparatus may also be useful as seen here. For e.g., by using an IgG-toxin conjugates specific for a cell surface epitope, where the toxin is a substrate that can be transported across an intact cell membrane, and which upon internalization could cause lineage-specific cell death of selective population and therefore its depletion, which may be useful which may be useful for a variety of applications. Other examples for cell depletion may include, but are not restricted to, HPRT system using toxic nucleoside analog 6-thioguanine (6-TG), prodrug-drug systems such as ganciclovir, divalent toxins, etc.

Therefore, as one of skill in the art will appreciate that in addition to the specific example described herein, there are other potential methods for live cell staining and detection. Without being bound by theory or the mechanism involved, these could include, live chromogenic alkaline phosphatase substrate; live gene reporters; live aldehyde dehydrogenase substrates including BAAA (BODIPY®—aminoacetate); live transporter efflux dyes like ABCG2; negative selection like lineage-specific epitope-drug constructs or antibody-toxin conjugates; molecular beacons; live cell proliferation and membrane potential dyes, etc. The mechanism of the preferential uptake by stem cells maybe known or unknown, and maybe specific to a particular specialized cell type besides stem cells.

Following identification and selection of a live stem cell by a suitable means (for example, by using the E-Z passage tool by Life Technologies, Inc.), the stem cells may be further expanded, or cultivated, and may be useful for downstream applications, including research, bioproduction of molecules of clinical interest, or for clinical applications.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

EXAMPLES

Example 1

Live Staining of ESC with FDP-AM and DDAOP-AM Esters

A steep challenge in stem cell research is the identification and characterization of cells. Commonly, surface antibodies are utilized but this method is often expensive and sterility is a concern. An ideal solution would be the use of nontoxic small molecules that are substrates for differentially expressed enzymes. One such exemplary substrate is alkaline phosphatase (enzyme), which is differentially expressed and its high activity is used as a measure of pluripotency. While alkaline phosphatase staining has been used to identify emerging pluripotent colonies during the process of somatic reprogramming, currently available alkaline phosphatase substrates are toxic to the cells and once stained cannot be propagated further. Here, novel live alkaline phosphatase substrates were developed using a modular synthesis platform.

Here, two test alkaline phosphate substrates, Fluorescein diphosphate-AM ester (FDP-AM) and DDAOP-AM ester were tested for live staining on pluripotent stem cells like H9 ESCs cultured on MEF (mouse embryonic fibroblast) feeder cells. H9 ESCs and other stem cells expressed high alkaline phosphatase. Negative control cells were MEFs and human dermal fibroblasts which express far lower levels of alkaline phosphatase.

A 10 mM substrate master stock solution (1000×) of fluorescein diphosphate-AM ester (FDP-AM) or DDAOP-AM was prepared (for FDP-AM for e.g., by adding 512.5 μL of tissue culture grade DMSO to 4 mg of the compound (MW: 780.52)).

Then, 100 μL of 10 mM FDP-AM or DDAOP-AM solution was diluted into 900 μL of DMEM to make 1 mM working stock; or 10 μM working stock was prepared by diluting 10 μl to 10 ml with 100 mM Tris-HCl pH 8.2 or DMEM basal media; or 1 μM working stock was prepared by diluting 10 μL of 1 mM working stock in 10 ml of DMEM, which was used.

The AP (alkaline phosphatase) live compound with concentrations ranging: >1 μM, 5 μM, 10 μM, 50 μM, 100 μM, and 200 μM, was made by adding 1, 5, 10, 50, 100 and 200 μL of 1 mM FDP-AM or DDAOP-AM working stock. Similarly, the AP live compounds with concentrations ranging: >20 nM, 50 nM, 100 nM, 250 nM, 500 nM, and 800 nM, was made by adding 2, 5, 19, 25, 50 and 80 μL of 1 μM FDP-AM working stock. The first dilution was added to an empty plate (no seeded cells) containing DMEM. The final concentration of the substrates, on the cells, were as follows: 50-200 nM for FDP-AM, and 50-200 μM for DDAOP-AM.

Incubation times were then determined, beginning with 90 seconds. Where no FITC expression was detected, expression was continued for up to 30 minutes. Levamisole was added to the wash buffer to quench the reaction. This step is whoever optional and not necessary. The samples were rinsed with DMEM and visualized.

In an exemplary embodiment, the novel live alkaline phosphatase substrate (dye) could be applied to adherent embryonic stem cells and/or pluripotent stem cells in culture and robust expression observed within 20-30 minutes. Staining was specific to pluripotent stem cells, and showed minimal background in MEF feeders and primary fibroblast cells. After removal of dye from the media, fluorescent labeled cells lost their signal within 60-90 minutes. The stained colonies could be further expanded without the loss of proliferation or pluripotency. This exemplary novel live alkaline phosphatase dye was further used to identify emerging pluripotent colonies from BJ human fibroblasts transduced with CytoTune™, a Sendaivirus based non-integrating reprogramming method. Clones were picked based on live alkaline phosphatase, and they expressed other pluripotent markers such as SSEA4 and TRA-1-60. Clones were propagated to over twelve passages, were karyotypically normal, and retained their pluripotency based on pluripotence marker expression and differentiation potential. Gene expression analysis of the iPSC lines showed expression patterns similar to a stem cell line, H9 ESC line, and was distinct from parental fibroblast cells.

These results indicated that the exemplary novel live alkaline phosphatase substrate detected pluripotent stem cells without altering its survival, proliferation or pluripotency. This tool could provide an easy to use, live monitoring method to track cells during reprogramming, or during routine cell culture of ESC and iPSCs.

Figure 2:
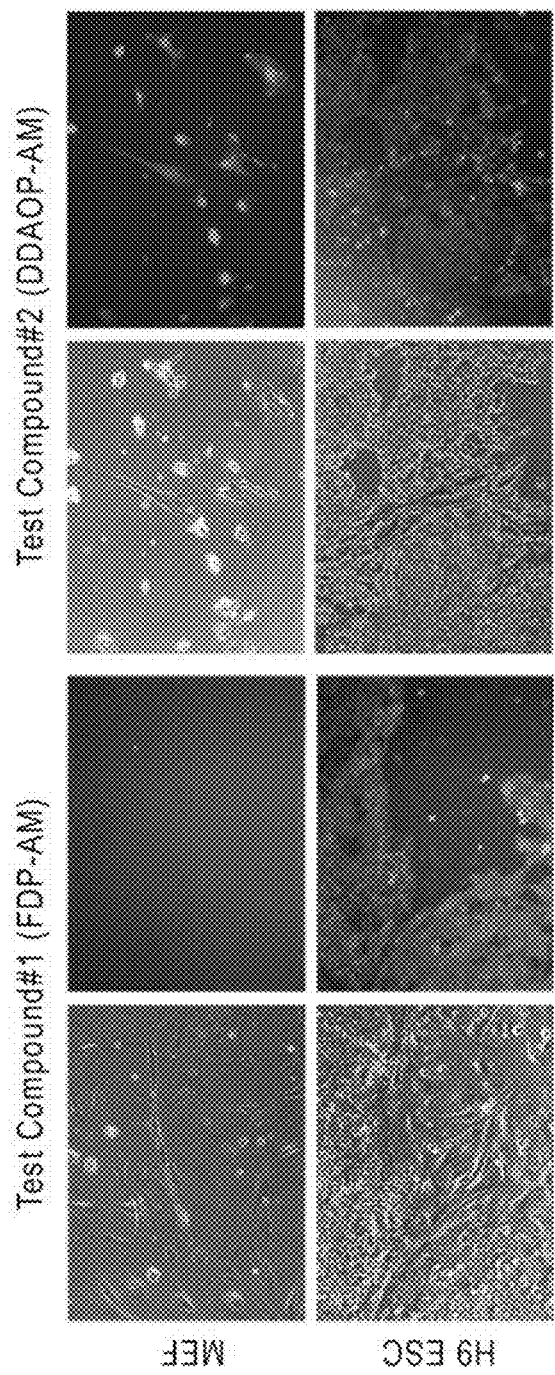
FIG. 2, left panel, shows robust staining of ESC colonies, with preserved morphology at 200 nM of FDP-AM and minimal background in the negative control MEFs. The right panel shows fluorescence of DDAOP-AM, with high background expression in MEF, while the stained ESCs show altered morphology.
Figure 3:
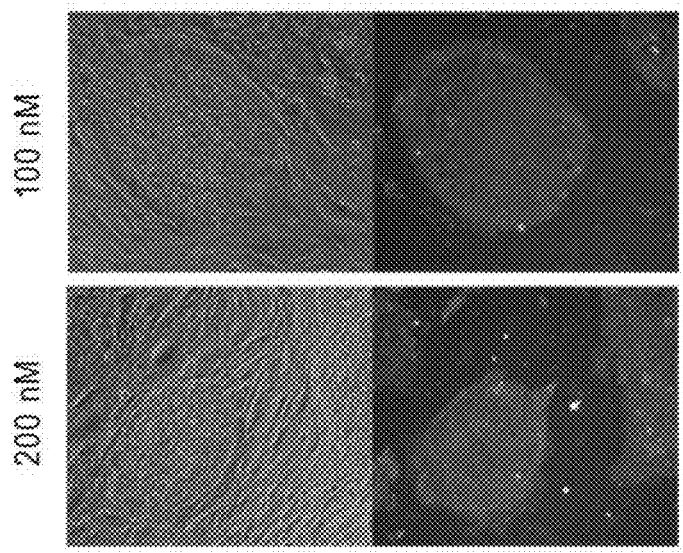
FIG. 3 shows stained ESC colonies cultured on MEF feeders stained with 100-200 nM FDP-AM for 30 minutes.
Figure 4:
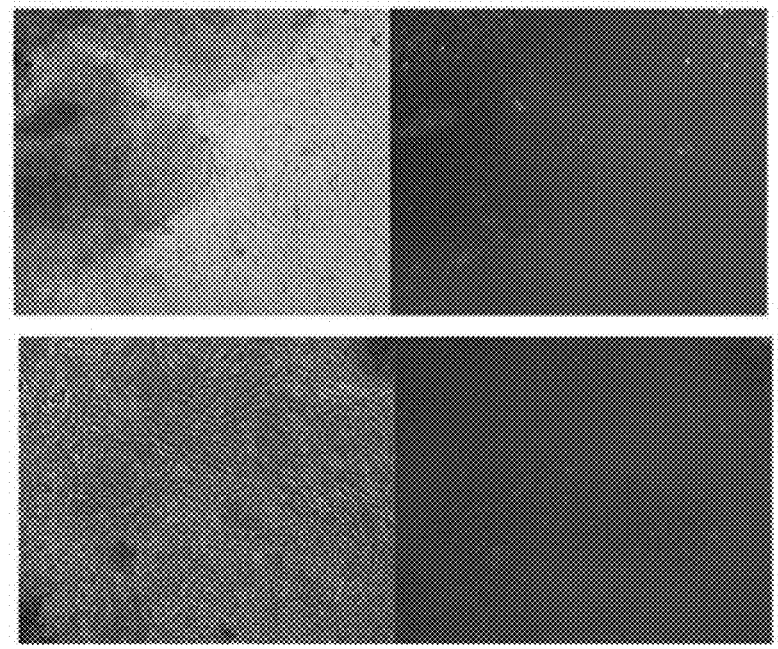
FIG. 4 shows that the fluorescent stain is completely removed from the stained cells seen in FIG. 3, when the media containing the substrate is removed and replaced with fresh ESC culture media.
Figure 5:
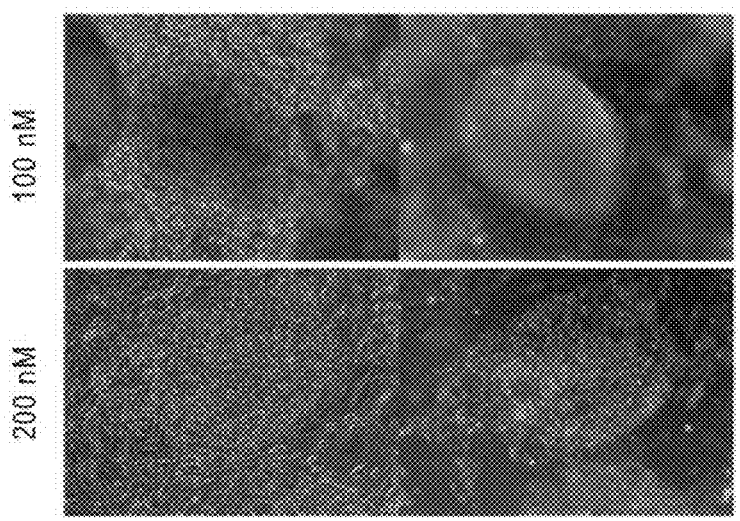
FIG. 5 shows that the cells in FIG. 4 retained their marker expression, and were successfully re-stained (after washing for dye removal, culturing cells overnight) with a second exposure for 30 min to FDP-AM the following day, again demonstrating positive fluorescent green staining.

Exemplary results can be seen in FIGS. 1-5. FIG. 1 shows fluorescence of FDP-AM in the nanomolecular range (left panel) and DDAOP-AM in the micromolar range (right panel), as described herein. FIG. 2 shows robust staining of the ESC colonies achieved at 200 nM for FDP-AM (left panel) or 200 µM for DDAOP-AM. FIG. 3 shows ESC colonies cultured on MEF feeders stained with 100-200 nM FDP-AM for 30 minutes. FDP-AM stained cells had normal morphology and continue to proliferate even after removal of the substrate, retain their cell-specific marker expression (left panel). DDAO-AM stained cells (right panel) showed higher background in negative control cells and altered morphology. FIG. 4 shows that the fluorescent stain is completely removed from the stained cells seen in FIG. 3, when the media containing the substrate is removed and replaced with fresh ESC culture media. FIG. 5 shows that the cells in FIG. 4 retained their marker expression, and were successfully re-stained with a second exposure to FDP-AM the following day, again demonstrating positive staining.

This demonstrates the successful staining with FDP-AM. This further demonstrates that the substrate diffuses out of the ESC within two hours. Additionally, this demonstrates that once the substrate diffuses out of the ESC, the cells are viable overnight and can be re-treated with the dye to achieve cell staining.

Figure 6:
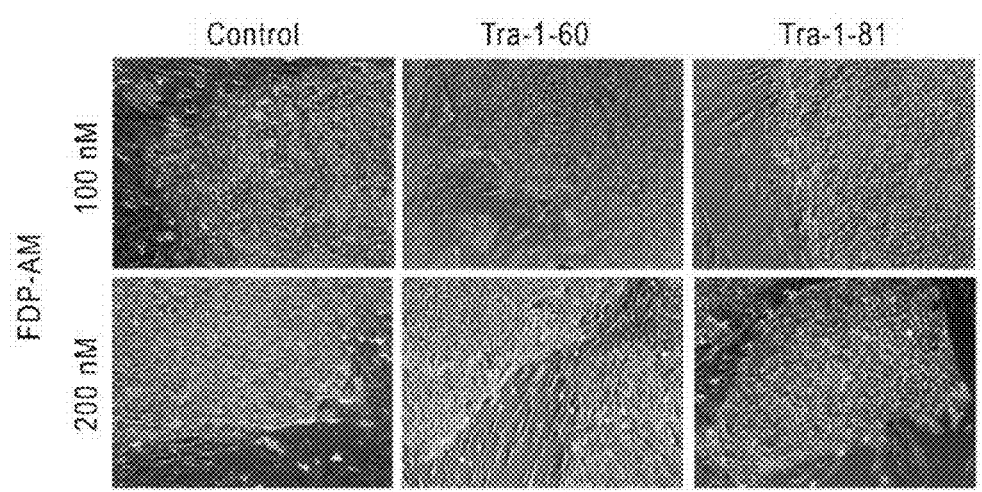
FIG. 6 shows ESCs on MEF feeders stained with FDP-AM (green) and primary antibody against pluripotent specific surface antigens Tra-1-60 and Tra-181 followed by secondary antibody conjugated to AlexaFluor 594 (Red).

Live alkaline phosphatase staining of ESC can be multiplexed with other staining methods such as immunochemical methods for pluripotent surface antigens using anti-Tra-1-60 and Tra-1-81 antibodies followed by secondary antibody conjugated to AlexaFluor 594 (red) (FIG. 6). Since both the methods are live staining methods, it offers an advantage of using two measures of pluripotency to characterize stem cell populations. Although the alkaline phosphatase enzyme is not highly specific, it serves as an enabling screen during iPSC generation workflow because alkaline phosphatase is the first pluripotent marker to appear during the process of reprogramming and undifferentiated human pluripotent stem cells express it strongly. Expression levels of alkaline phosphatase decreases following stem cell differentiation. FDP-AM staining in combination with ESC morphology and colony size determination can be indicative of identity and emerging iPSC colonies.

Figure 7:
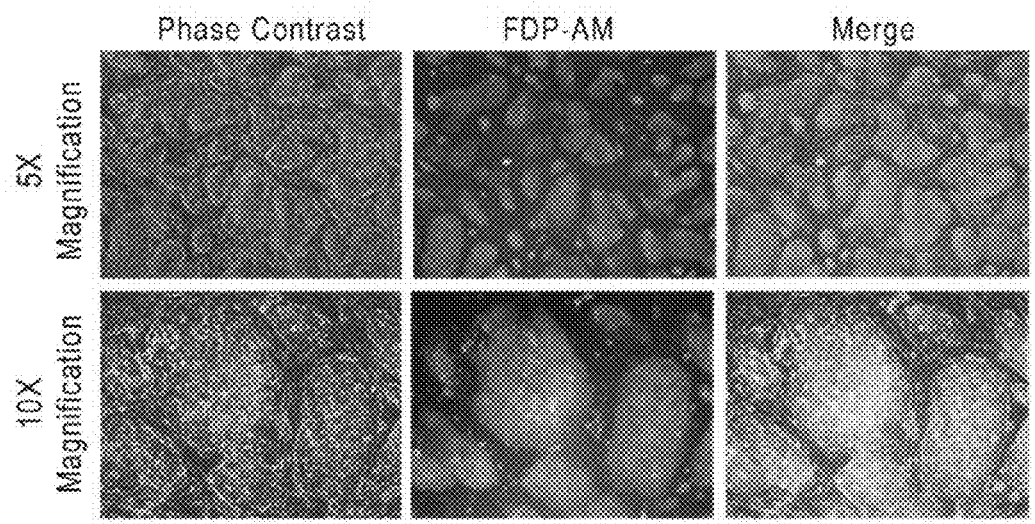
FIG. 7 shows mouse ESCs on MEF feeders treated with 200 nM FDP-AM (green) for 30 min. mESC colonies show robust staining with little or no background in the MEF feeder cells.

Alkaline phosphatase is not specific just for human ESCs but also for murine ESCs. FDP-AM specially stains mESC with green fluorescent byproduct of FDP-AM following alkaline phosphatase mediated conversion with minimal background staining of the MEF feeders. The fluorescent signal is robust and visible at lower 5× magnification [FIG. 7].

Figure 8:
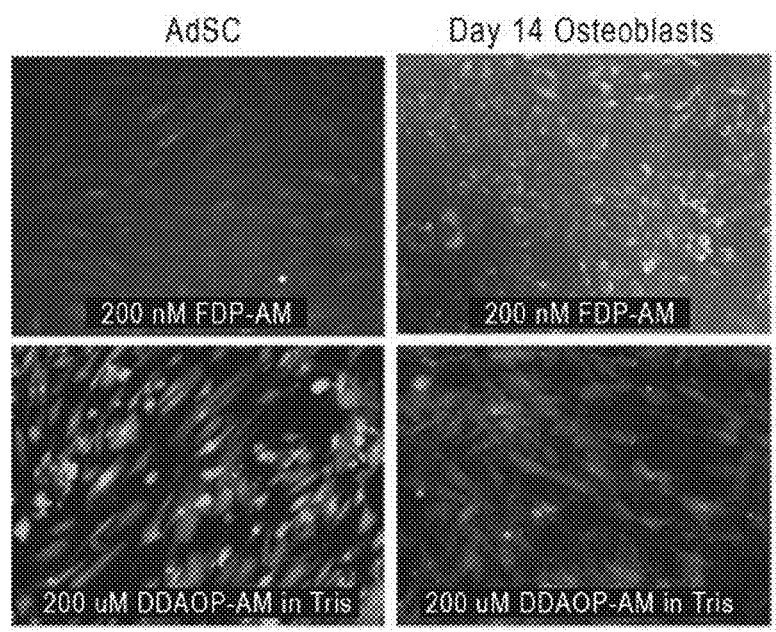
FIG. 8 shows adipose derived mesenchymal stem cells (AdSCs) (left panel), and AdSCs differentiated into osteoblasts (right panel) stained with FDP-AM (top panel) or DDAOP-AM (bottom panel). DDAOP-AM does not show specific staining as it stains both parent AdSC and osteoblasts. FDP-AM, on the other hand, shows specific staining for the differentiated phenotype (osteoblast) but not in AdSCs.

Alkaline phosphatase is also expressed at high levels in differentiating osteoblasts and mature osteocytes. Test compound 1, FDP-AM showed specific staining of differentiating osteoblasts with minimal background in its parental undifferentiated MSC while Test compound 2 DDAOP-AM failed to show specific staining and exhibited high levels of staining in both parent MSC and differentiated osteoblasts [FIG. 8].

These results show that production of fluorescein-di-phosphate which is nonfluorescent, but a substrate for alkaline phosphatase differentially expressed in some cell types. Fluorescein-di-phosphate is catalyzed down to the end-product fluorescein in alkaline phosphatase expressing cells thus staining those cells green fluorescent. Since fluorescein is a small nontoxic molecule, it does not affect the viability or morphology of the stained cells and easily diffuses out of the cells within a few hours. These results indicate that this exemplary novel live alkaline phosphatase substrate offers a simple and easy tool, not only to identify pluripotent colonies, but also to further propagate the identified colony. For instance, this tool provides an easy live monitoring method to track cells during reprogramming, or during routine culture of ESC and iPSC cells.

Figure 9:
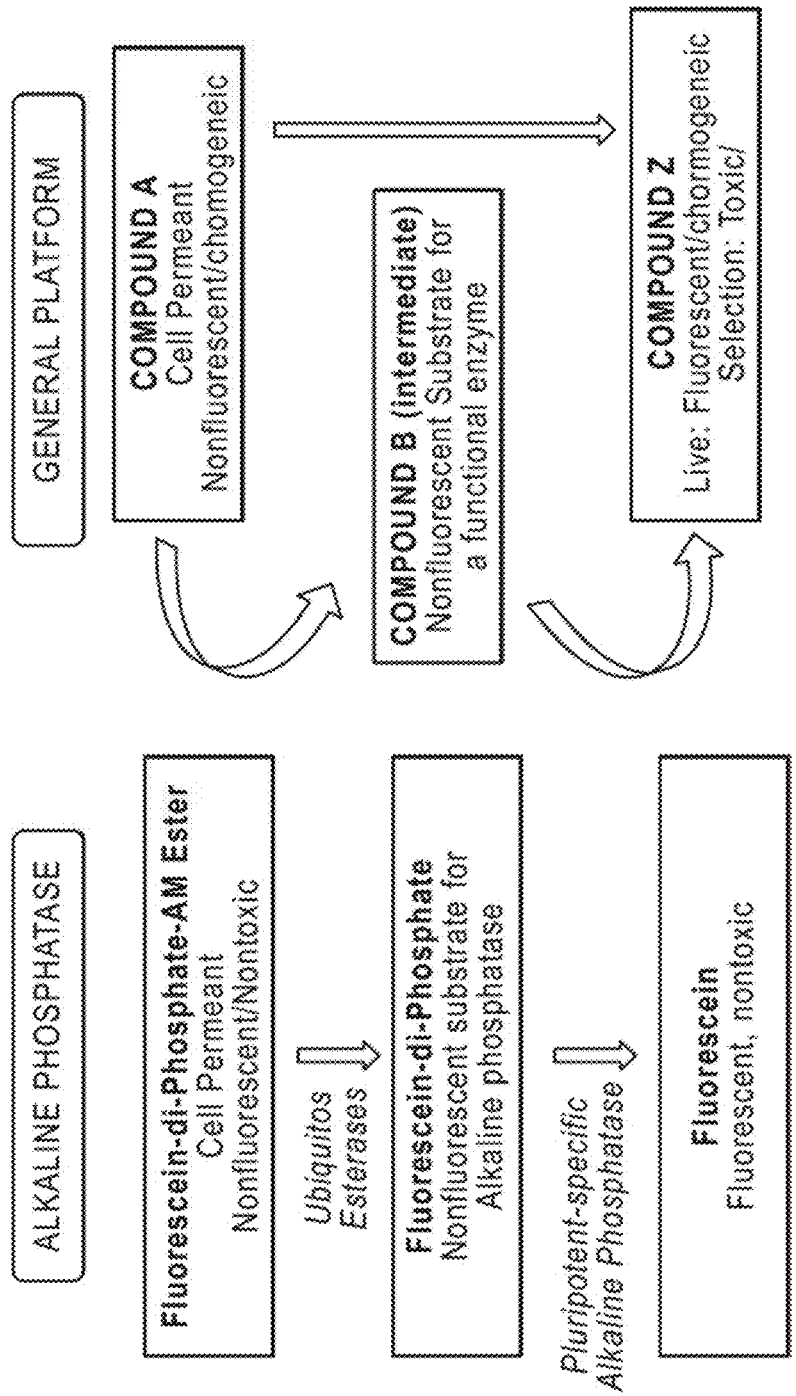
FIG. 9 shows an outline of a platform approach to develop live dyes for staining differentially expressed functional molecules in cells.

The concept outlined in FIG. 9 exemplifies the platform approach to develop live dyes for differentially expressed functional molecules in cells. The premise is that the parent compound, like a dye, should have chemical moieties that enable easy entry through the cell membrane. Once inside the cells, the compound is a direct substrate to a functional molecule, including but not limited to an enzyme, or requires additional processing to become functional, by any ubiquitous or cell-specific molecule to generate a final product that can be specifically utilized, or specifically selected, or specifically detected. Specific staining of iPSCs and/or ESCs using the exemplary, novel live alkaline phosphatase substrate is an example.

Following identification and selection of a live stem cell by a suitable means (for example, by using the E-Z passage tool by Life Technologies, Inc.), the stem cells may be further expanded, or cultivated, and may be useful for downstream applications, including research, bioproduction of molecules of clinical interest, or for clinical applications.

The examples were intended to illustrate, but not limit, certain embodiments of the invention. One skilled in the art will understand that various modifications are readily available and can be performed without substantial change in the way the invention works. All such modifications are specifically intended to be within the scope of the invention claimed herein.

What is claimed is:

1. A composition comprising a substrate contacted with a live stem cell, wherein the substrate is cell permeable and is capable of being modified by an enzyme specific to the live stem cell into a modified substrate, wherein the modified substrate is both permeable and detectable such that the live stem cell can be identified by detecting the presence of the modified substrate, wherein the substrate and the modified substrate are non-toxic, and wherein the substrate is a xanthene derivative, the xanthene derivative is a fluorescein derivative, the fluorescein derivative is a fluorescein diphosphate and the fluorescein diphosphate has the structure of formula II:

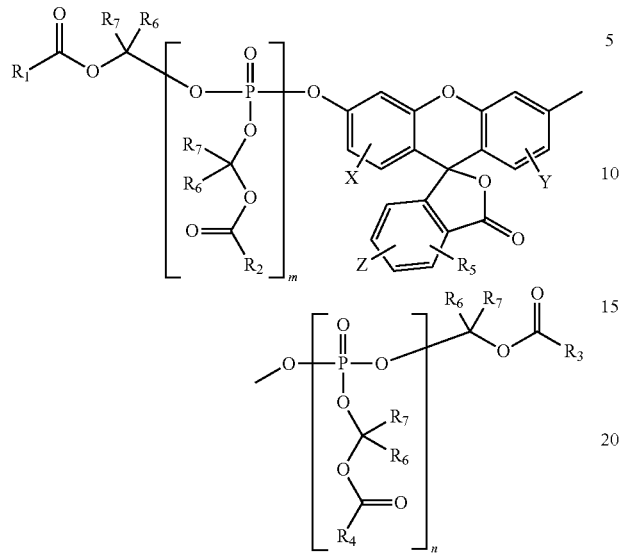

where:

R1, R2, R3, and R4 are individually chosen from alkyl, aryl, aralkyl, heteroaryl, and heteroaralkyl;

R6 and R7 are individually chosen from H, alkyl, aryl, aralkyl, heteroaryl, and heteroaralkyl;

X and Y are individually chosen from H, halogen, amino alkoxy, SH, SR, alkyl, aryl, aralkyl, heteroaryl, and heteroaralkyl;

Z and R5 are individually chosen from H, COOH, COOR, OH, amino, alkoxy, halogen, alkyl, aryl, aralkyl, heteroaryl, and heteroaralkyl;

and m and n individually range from 1 to 3.

2. The composition according to claim 1, wherein the enzyme specific to the live stem cell is an acid or alkaline phosphatase.

3. The composition according to claim 1, wherein the substrate is fluorescein diphosphate-AM ester of formula III:

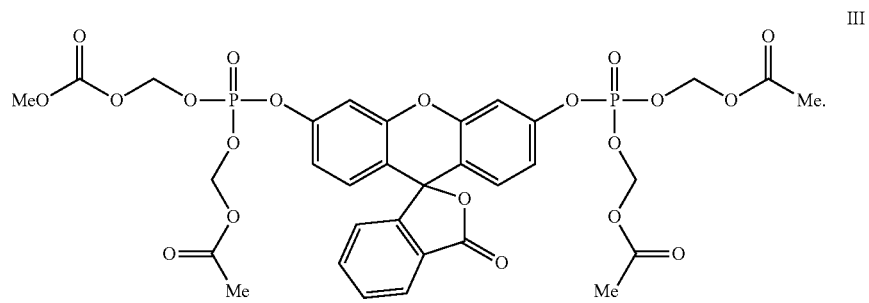 [SMILES: COC(=O)OCOP(=O)(OCOC(C)=O)Oc1ccc2c(c1)Oc1cc(OP(=O)(OCOC(C)=O)OCOC(C)=O)ccc1C21OC(=O)c2ccccc21]

4. The composition of claim 1 wherein the live stem cell is selected from the group consisting of an embryonic stem cell (ESC), an induced pluripotent stem cell (iPSC), a pluripotent cell, a progenitor cell, a reprogrammed cell, and a dedifferentiated cell.

5. The composition of claim 1 wherein detecting the presence of the modified substrate comprises detecting a fluorescent signal.

* * * * *

UNITED STATES PATENT AND TRADEMARK OFFICE
CERTIFICATE OF CORRECTION

PATENT NO.        : 9,334,523 B2
APPLICATION NO.   : 13/985559
DATED             : May 10, 2016
INVENTOR(S)       : Uma Lakshmipathy et al.

Page 1 of 1

It is certified that error appears in the above-identified patent and that said Letters Patent is hereby corrected as shown below:

In the claims,

In Column 29, under claim 1, structure II should be depicted on one line with no interruptions. Please replace structure II with the following:

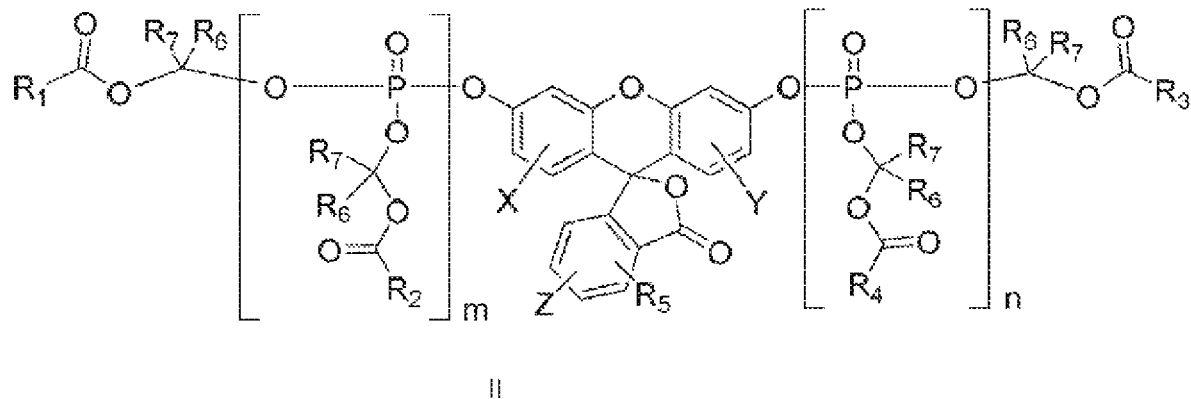

II

Signed and Sealed this
Ninth Day of August, 2016

Michelle K. Lee
*Director of the United States Patent and Trademark Office*